United States Patent [19]

Guerra

[11] 4,106,491

[45] * Aug. 15, 1978

[54] DEVICE FOR PROLONGED INTRAVASCULAR INFUSION

[76] Inventor: Luis A. Guerra, Apt. 3A, 239 Central Park West, New York, N.Y. 10024

[*] Notice: The portion of the term of this patent subsequent to Dec. 14, 1993, has been disclaimed.

[21] Appl. No.: 749,948

[22] Filed: Dec. 13, 1976

Related U.S. Application Data

[63] Continuation-in-part of Ser. No. 598,902, Jul. 24, 1975, Pat. No. 3,996,923, and a continuation-in-part of Ser. No. 344,387, Mar. 23, 1973, Pat. No. 3,906,930.

[51] Int. Cl.² .............................................. A61B 5/00
[52] U.S. Cl. .................................. 128/2 F; 128/214 R
[58] Field of Search .................. 128/2 F, 2 B, 214 R, 128/214.4, 218 R, 218 NV, 218 N, 218 D, 215, 276, 274, 221

[56] References Cited

U.S. PATENT DOCUMENTS

| | | | |
|---|---|---|---|
| 3,143,109 | 8/1964 | Gewertz | 128/276 X |
| 3,181,529 | 5/1965 | Wilburn | 128/DIG. 5 |
| 3,416,567 | 12/1968 | Von Dardel et al. | 128/274 X |
| 3,460,529 | 8/1969 | Leucci | 128/2 F |
| 3,513,829 | 5/1970 | Deuschle et al. | 128/276 X |
| 3,585,996 | 6/1971 | Reynolds et al. | 128/221 X |
| 3,753,432 | 8/1973 | Guerra | 128/DIG. 5 |
| 3,906,930 | 9/1975 | Guerra | 128/2 F |
| 3,996,923 | 12/1976 | Guerra | 128/2 F |

FOREIGN PATENT DOCUMENTS

| | | | |
|---|---|---|---|
| 1,054,174 | 10/1953 | France | 128/221 |
| 532,192 | 8/1931 | Fed. Rep. of Germany | 128/DIG. 5 |
| 743,839 | 1/1956 | United Kingdom | 128/218 D |

*Primary Examiner*—John D. Yasko
*Attorney, Agent, or Firm*—Blum, Moscovitz, Friedman & Kaplan

[57] ABSTRACT

An improved device for the introduction of fluids into blood vessels, and, particularly, into veins, includes a cannula-containing portion fitted with a valve which is normally closed. A connector portion can be connected to a source of fluid such as IV, special medication or alimentation. The connector portion is so shaped that it can be joined tightly to the cannula-containing portion, simultaneously and automatically opening the valve so that fluid can pass in sequence through the connector portion and through the cannula. A metal cannula can be used where fluid is to be supplied for moderate periods such as a few hours. Where fluid is to be supplied for longer periods, provision is made for introduction into the blood vessel of a cannula of a plastic which is low in thrombogenicity and tendency to cause phlebitis.

12 Claims, 5 Drawing Figures

DEVICE FOR PROLONGED INTRAVASCULAR INFUSION

CROSS REFERENCE TO RELATED APPLICATIONS

The present application is a continuation-in-part application of my co-pending Application having the Ser. No. 598,902, now U.S. Pat. No. 3,996,923, itself a Continuation-In-Part of Application having the Ser. No. 344,387, now U.S. Pat. No. 3,906,930.

BACKGROUND OF THE INVENTION

In my previous patents I disclosed a device for taking blood samples from patients by the use of evacuated containers attached through a connector which could be joined to a body holding a metal cannula. The body holding the metal cannula was referred to as a support portion and was fitted with a valve which was normally closed but which opened on making connection between the support portion and the connector to the evacuated container.

While the possibility of using the support portion for the introduction of medication into a patient was disclosed, the technique by which such introduction was to be effected was not such as to make it convenient to allow the cannula to remain in the vein of a patient for periods as long as several days. In view of the fact that procedures requiring the presence of a cannula or a catheter in the vein of a patient for extended periods are now becoming common, it is evident that there is a need for a device by which such procedures can be carried out conveniently, effectively and safely. The device should make it easy to change and control the fluids being fed to the patient and should also be relatively inexpensive. Further, it would be desirable that said support portion be useable in the manner disclosed in my previous patents, namely, for taking of one or more blood samples without repeated puncture of the individual.

A most important point is the present techniques for introducing fluid into a vein or other blood vessel require connection of a source of fluid to a cannula after emplacement of the cannula in the blood vessel. Under such circumstances there is always some loss of blood from the maximal end of the cannula, an undesirable feature.

SUMMARY OF THE INVENTION

A device for the intravascular infusion of selected fluids includes a support portion and a connector portion. The support portion has a passage therethrough with a valve at the proximal end thereof and a cannula at the distal end thereof. The support portion also includes an aperture making a junction with the passage, the junction normally being closed by the valve. Where the cannula is to remain in a blood vessel for only moderately long periods of time, the cannula is preferably of metal. Where the cannula is to remain for extended periods of time in the blood vessel the cannula is of a plastic which is non-thrombogenic and low in tendency to cause phlebitis.

A connector portion has a distal end designed to enter the aperture of the support portion in a first orientation and open the valve when rotated into a second orientation, simultaneously sealing the join between the connector and support portions. The proximal end of the connector portion, preferably, is initially closed with a plug which fits sufficiently tightly to prevent flow of blood around same but not to prevent flow of air. Insertion of the cannula into a vein with the connector portion in place and in said second orientation results in flow of blood through the cannula, through the aperture in the support portion and through the connector up to the plug, the portion of the connector immediately upstream from the plug serving as a flush chamber for removal of air. At this point, the connector is rotated to close the valve in the support portion, the plug can be removed without loss of blood and connection made to a source of fluid, after which the connector is rotated back to open the valve.

In general, the cannula is of metal, but in a second embodiment of the invention, the cannula is of a plastic having low thrombogenicity and low tendency to cause phlebitis. The plastic cannula is introduced into a blood vessel through the use of a second cannula of metal which is introduced through the plastic cannula, this introduction being possible because of the fact that the valve is a hollow stopper which can be penetrated by a metal cannula. After the plastic cannula is in place in a blood vessel, the metal cannula is withdrawn through the valve.

The metal cannula may be tubular and may have a lateral orifice therein to permit blood entering the metal cannula to emerge therefrom into the passage through the support portion. Alternatively, the metal cannula may be slotted at least to an extent such that blood entering the metal cannula can flow into the same aperture.

Accordingly, an object of the present invention is an inexpensive and convenient device for feeding fluid such as IV fluid, medications and nourishment to a patient for extended periods of time.

A further object of the present invention is an inexpensive and convenient device for supplying fluids intravascularly to a patient where the fluid being supplied may be changed without repeated puncture of the blood vessel into which the fluids are to be introduced.

A significant object of the present invention is a device for introduction of fluid intravascularly where introduction of a cannula and subsequent connection to a source of fluid can be effected without loss of blood.

An important object of the present invention is an inexpensive and convenient device for supplying fluids intravascularly to a patient and which can also be used for taking blood.

Still other objects and advantages of the invention will in part be obvious and will in part be apparent from the specification.

The invention accordingly comprises an article of manufacture possessing the features, properties, and the relation of elements which will be exemplified in the article hereinafter described, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 1:
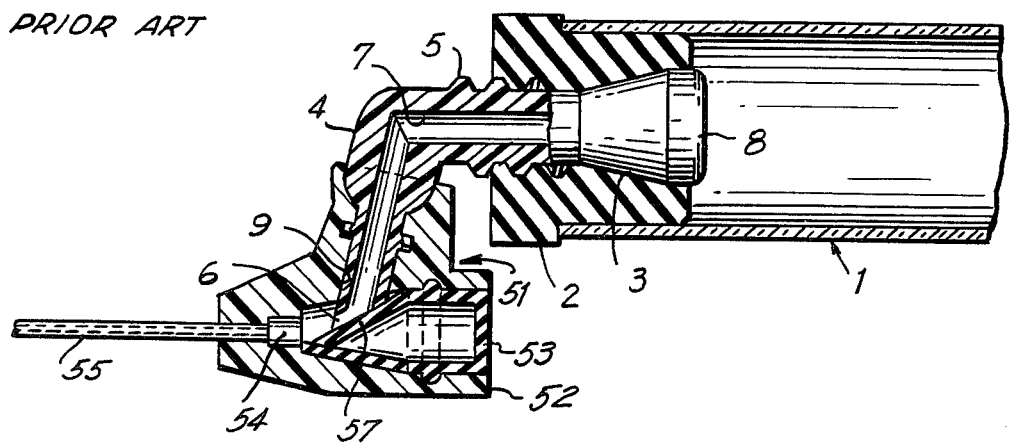
FIG. 1 shows a blood-taking device in accordance with the prior art, the support portion thereof having points of similarity with the support portion of the device in accordance with the present invention.

As shown in FIG. 1, an evacuated container portion represented generally by the reference numeral 1 is fitted with a stopper 2 through which passes a connector 4 having a thread 5. The connector 4 has a passage 7 therethrough which is sealed at the proximal end 8 thereof and which has a lateral orifice 3. Rotating the container portion 1 in clockwise direction as viewed from the right moves the container to the left, making connection between passage 7 and the interior of the container through lateral orifice 3.

Connector 4 has a distal end 6 which mates sealingly with aperture 9 of support portion 51. Support portion 51 is sealed at the proximal end 52 by hollow stopper 53. Hollow stopper 53 rests in passage 54 which connects with cannula 55. Stopper 53 is long enough so that it normally seals the junction between aperture 9 and passage 54. Insertion of distal end 6 of connector 4 into aperture 9 depresses side wall 57 of stopper 53 and connects aperture 9 with passage 54 for flow of blood therethrough and then into container 1.

Figure 2:
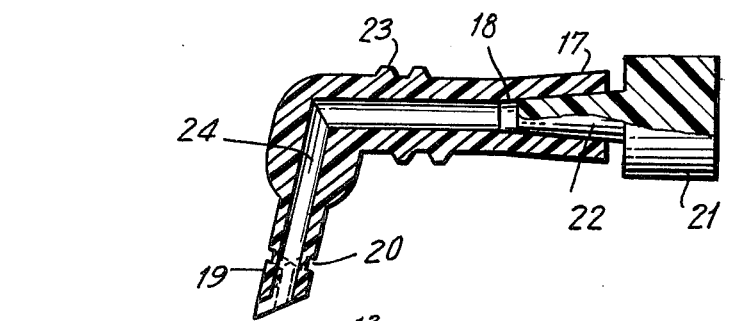
FIG. 2 is an embodiment of the present invention in exploded form.

In the embodiment shown in FIG. 2, distal end of connector portion 17 is introduced into support portion 10 with the two portions at right angles to each other. A seal therebetween is effected and the valve consisting of hollow stopper 12 is opened when connector portion 17 is rotated into alignment with support portion 10. The valve may also be a stopper of a closed-cell flexible foam. In such an embodiment, the stopper need not be hollow, but instead may be "solid". A suitable foam may be polyurethane.

The support portion of the present invention, in the embodiment shown in FIG. 2, is similar to that of the prior art in most of its features. Plastic body 11 has a passage 15 therethrough connecting with hollow metal cannula 16. Hollow stopper 12, preferably of rubber, is seated in the proximal end of passage 15 and, in normal position, closes the junction between aperture 13 and passage 15. Hollow stopper 12 is conveniently closed at its proximal end, but may equally well be closed instead at its distal end. In a preferred form, connector portion 17 is sealingly joined to the support portion, indicated generally by the reference numeral 10, by means of ribs 14 on the interior of aperture 13 and threads 20 on the distal end 19 of connector portion 17. The seal may be established in the embodiment shown by rotating the connector portion into alignment with the support portion after insertion of distal end 19 into aperture 13.

The connector portion 17 is shown with exterior thread 23, this thread being irrelevant to the transfer of fluid through passage 24 in connector portion 17. The thread is present because the connector portion can also be used in connection with the blood-taking device shown in FIG. 1. In a preferred form of the present invention the proximal end 22 of connector portion 17 is tapered, providing a tapered socket 18 therein. Plug 21, preferably of plastic, fits tightly enough within tapered socket 18 to prevent flow of blood between plug and socket but not tightly enough to prevent flow of air therethrough. Consequently, the proximal end of the connector can serve as a flush chamber for displacement of air from the system, when cannula 16 is inserted into a blood vessel. When blood reaches plug 21, the connector portion 17 is rotated so as to close the valve consisting of stopper 12 in passage 24. The flow of blood is thus halted, at which point plug 21 can be removed from tapered socket 18 and connection made at socket 18 to a source of fluid without loss of blood. After effecting connection to a source of fluid, connector portion 17 is rotated back into alignment with support portion 10 to open the hollow stopper valve and make possible flow of fluid.

The metal cannula can be allowed to remain in a blood vessel for no longer than a period of a few hours. Accordingly, where it is desired to feed fluid to a patient over longer periods of time such as up to several days, plastics which are essentially non-thrombogenic and low in tendency to cause phlebitis are preferred as the material for the cannula. A suitable material is Teflon.

Figure 3:
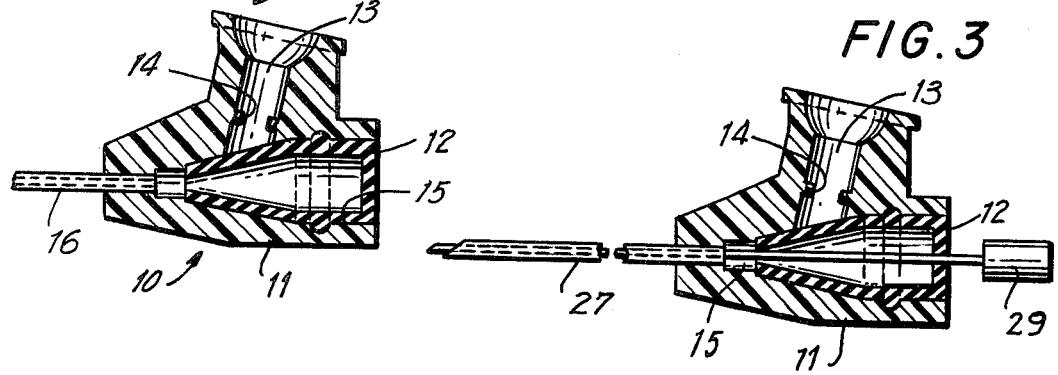
FIG. 3 is another embodiment of the present invention.

The technique for inserting a plastic cannula as used in connection with conventional catheters is well known. This technique is adaptable to the present device. As shown in FIG. 3 a plastic cannula 27 fits tightly within body 11. A metal cannula 28 is inserted through hollow stopper 12 and through plastic cannula 27, the length of the metal cannula being such that the tip thereof protrudes slightly beyond the tip of cannula 27. To introduce the plastic cannula into a blood vessel, the puncture is made with the tip of the metal cannula 28. The plastic cannula 27 fits sufficiently tightly about the metal cannula 28 so that the tip of the plastic cannula can enter through the puncture and come to rest within the blood vessel.

The insertion into the blood vessel is preferably made with connector portion 17 joined to support portion 10. Blood flows through the annulus between the two cannulas and up through aperture 13 and passage 24 as far as plug 21, displacing all air from the device in the process.

Figure 4A:
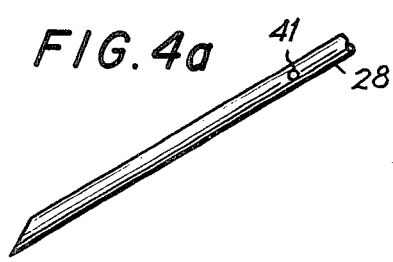
FIGS. 4a and 4b are embodiments of metal cannulas for use in combination with the support portion shown in FIG. 3.
Figure 4B:
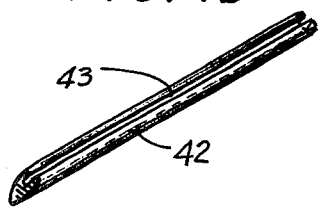

The rate of flow of blood between the two cannulas is relatively low since it is desirable that they make a close fit with each other. Accordingly, as shown in FIG. 4a the metal cannula 28 may have an aperture 41 therein through which blood entering the metal cannula may exit into passage 15. For this purpose, the aperture 41 should lie within passage 15 when the metal cannula is in position for insertion into a blood vessel. Alternatively, the cannula may be slotted as shown in FIG. 4b, the slot 43 extending back into passage 15.

Preferably, the proximal end of metal cannula 28 is closed off at the proximal end as with a plastic handle 29. Alternatively, the proximal end of said cannula may have a standard fitting thereon to take a conventional syringe for introduction of medication into a blood vessel or withdrawal of a blood sample.

In the blood-taking device of FIG. 1 the proximal end of the connector portion has therein a lateral orifice 3 which, in combination with stopper 2, functions as a valve. Preferably this lateral orifice is not provided in the connector portion of the present device. However, the omission of this orifice does not alter the possibility of using the same mold for both types of connectors; it is only necessary to remove a pin from the mold in order to eliminate the orifice. As a result, a substantial economy is provided through the fact that both the support portion and the connector portion for the blood-taking device and the fluid-feeding device can be made in the same mold.

It will thus be seen that the objects set forth above, among those made apparent from the preceding description, are efficiently attained and, since certain changes may be made in the above article without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An improvement in a device for introducing fluids into a blood vessel over extended periods of time, comprising a support portion removably and sealingly connectable with a source of intravenous fluid, of medication in solution or of alimentation in solution, said support portion comprising a body having a passage therethrough and an aperture connecting with said passage and forming a junction therewith, valve means at the proximal end of said passage and normally closing said aperture at said junction, and a cannula, the proximal end of said cannula being tightly sealed in the distal end of said passage, said valve means being operable by exertion of mechanical force through said aperture.

2. The device of claim 1, further comprising a connector portion having a passage therethrough, said connector portion having a distal end shaped for fitting sealingly within said aperture in said body portion and opening said valve means on insertion of said distal end of said connector portion into said aperture for effecting sealed connection between said support and connector portions.

3. The device of claim 2, further comprising a plug means shaped to fit tightly enough within the proximal end of said passage in said connector portion to prevent the flow of blood around said plug means but not so tightly as to prevent escape of air around said plug means.

4. The device of claim 2, wherein the proximal end of said connector portion is shaped for connecting sealably and removably to an external source of fluid.

5. The device of claim 1, wherein said cannula is of metal and has a sharp distal end suitable for carrying out venopuncture.

6. The device of claim 1, wherein said cannula is of a plastic of low thrombogenicity and low tendency to cause phlebitis, said passage has an axis, said cannula has an axis, said axes being essentially colinear, and a metal cannula of length great enough to traverse said body portion and project sufficienty beyond the distal end of said plastic cannula so as to carry said plastic cannula therewith on insertion of said metal cannula into a blood vessel, the proximal end of said metal cannula being sealed.

7. The device of claim 6, wherein said metal cannula has a lateral opening so disposed that when said metal cannula is in place in said body portion and plastic cannula and inserted into a blood vessel, any blood entering said metal cannula can escape through said opening in same into said aperture in said support portion.

8. The device of claim 6, wherein said metal cannula has a lateral slot therein extending from the distal end thereof toward the proximal end thereof by a distance such that when said metal cannula is in position within said support portion and plastic cannula and inserted into a blood vessel, any blood flowing in the proximal direction through said cannula can reach said aperture in said support portion.

9. The device of claim 2, wherein said connector portion and said support portion join together by means of a bayonet lock, the rib portion of said lock being disposed within said aperture of said support portion and the thread portion of said bayonet lock being disposed on said connector portion.

10. The device of claim 1, wherein said valve means is a hollow stopper closed at an end thereof, said closed end sealing the proximal end of said passage in said support portion and the side wall of said hollow stopper sealing the junction between said aperture and said passage in said support portion in the absence of an external force exerted through said aperture, said hollow stopper being of a material which is flexible, which can be penetrated by a metal cannula and which will close sealingly around the point of penetration subsequent to removal of said metal cannula therefrom.

11. The device of claim 10, wherein said hollow stopper is of rubber.

12. The device of claim 1, wherein said valve means is a stopper of a closed-cell flexible foam.

* * * * *